United States Patent [19]

Liebetruth

[11] Patent Number: 4,570,264
[45] Date of Patent: * Feb. 11, 1986

[54] TOMOGRAPHIC X-RAY APPARATUS FOR THE PRODUCTION OF TRANSVERSE LAYER IMAGES

[75] Inventor: Reiner Liebetruth, Erlangen, Fed. Rep. of Germany

[73] Assignee: Siemens Aktiengesellschaft, Berlin & Munich, Fed. Rep. of Germany

[*] Notice: The portion of the term of this patent subsequent to Nov. 13, 1996 has been disclaimed.

[21] Appl. No.: 561,677

[22] Filed: Dec. 15, 1983

Related U.S. Application Data

[63] Continuation-in-part of Ser. No. 53,263, Jun. 29, 1979, abandoned, and a continuation-in-part of Ser. No. 320,737, Nov. 12, 1981, Pat. No. 4,447,922, which is a continuation of Ser. No. 53,263, Nov. 12, 1981, abandoned, said Ser. No. 53,263, is a continuation-in-part of Ser. No. 775,452, Mar. 8, 1977, Pat. No. 4,174,481.

[30] Foreign Application Priority Data

Mar. 31, 1976 [DE] Fed. Rep. of Germany ....... 2613809

[51] Int. Cl.$^4$ ............................................. G03B 41/16
[52] U.S. Cl. .......................................... 378/20; 378/4
[58] Field of Search .......................... 378/19, 20, 146, 4

[56] References Cited

U.S. PATENT DOCUMENTS

| | | |
|---|---|---|
| 3,101,407 | 8/1963 | Shipman, Jr. . |
| 3,780,291 | 12/1973 | Stein et al. .................... 250/363 |
| 3,974,388 | 8/1976 | Distler et al. ................ 250/445 T |
| 4,045,672 | 8/1977 | Watanabe . |
| 4,051,379 | 9/1977 | Zacher ................................. 378/7 |
| 4,174,481 | 11/1979 | Liebetruth ................... 250/445 T |
| 4,477,922 | 10/1984 | Liebetruth . |

FOREIGN PATENT DOCUMENTS

| | | |
|---|---|---|
| 2237272 | 2/1974 | Fed. Rep. of Germany . |
| 2613809 | 10/1977 | Fed. Rep. of Germany . |
| 1561969 | 2/1969 | France . |
| 2052548 | 4/1971 | France . |
| 2145325 | 2/1973 | France . |
| 2163959 | 7/1973 | France . |

OTHER PUBLICATIONS

"Localization with the EMI Scanner", Norman et al., Dec., 1975.
Bowley, et al., "A Radioisotope Scanner for Rectilinear, Arc. Transverse Section and Longitudinal Section Scanning: (ASS-The Aberdeen Section Scanner)" British Journal of Radiology, vol. 46, 1973, pp. 262-271.
Norman, et al., "Localization with the EMI Scanner" American Journal of Radiology, vol. 125, No. 4, Dec. 1975, pp. 961-964.
Haaga, et al., "CT Longitudinal Scan" American Journal of Roentgenology, vol. 127, 1976, pp. 1059-1060.
Kuhl, et al., "Transmission Scanning," *Radiology,* vol. 87, Aug. 1966, pp. 278-284.

*Primary Examiner*—Craig E. Church
*Attorney, Agent, or Firm*—Hill, Van Santen, Steadman & Simpson

[57] ABSTRACT

In order to facilitate exact positioning of a patient relative to tomographic X-ray apparatus the patient is moved longitudinally of the apparatus and the apparatus is retained in a limited angular relationship and operated to automatically produce successive sets of transmittance readings to define a radiographic image having a longitudinal extent sufficient to encompass the precisely desired region of the patient for which a tomographic image is to be generated. The stored sets of readings may be reproduced on a conventional television display unit along with suitable reference means coordinated with the patient's longitudinal position in the apparatus. The radiograph even though taken in a single angular relationship can still provide sufficient information to permit selection of the precise desired patient longitudinal position relative to the tomographic apparatus, whereupon the tomographic apparatus is operated in the usual manner for scanning of the selected transverse layer over a wide range of angles but with a fixed relative longitudinal relationship to the patient still scans a substantial portion of the patient cross section, the sets of readings for successive patient sections, e.g. offset by one millimeter, being stored in digital form, and utilized for on line display of a radiograph covering the desired longitudinal extent.

37 Claims, 2 Drawing Figures

TOMOGRAPHIC X-RAY APPARATUS FOR THE PRODUCTION OF TRANSVERSE LAYER IMAGES

CROSS-REFERENCE TO RELATED APPLICATIONS

The present application is a continuation-in-part of my pending application Ser. No. 053,263 filed June 29, 1979, now abandoned and Ser. No. 320,737 filed Nov. 12, 1981, now U.S. Pat. No. 4,447,922 issued Oct. 16, 1984, said application Ser. No. 320,737 being a continuation application based on Ser. No. 053,263, and said application Ser. No. 053,263 being a continuation-in-part of my application for patent U.S. Ser. No. 775,452 filed Mar. 8, 1977, now U.S. Pat. No. 4,174,481 issued Nov. 13, 1979. The disclosure of said U.S. Pat. No. 4,174,481 is incorporated herein by reference.

BACKGROUND OF THE INVENTION

This invention relates to a tomographic X-ray apparatus for the production of transverse layer images of an exposed object, consisting of a patient's support, an X-ray measuring arrangement with an X-ray source, which generates a bundle of X-rays penetrating the exposed object and of which the cross sectional extent perpendicular to the plane of the layer is equal to the thickness of the layer, for example, and a radiation receiver which ascertains the radiation intensity beyond the object by scanning the projected bundle of rays, and a driving device for the measuring arrangement including a pivot mounting for accommodating rotational movements of the X-ray measuring arrangement, the apparatus further including a measurand converter for the conversion of the signal supplied by the radiation receiver into a tomographic image.

For detecting the layer image, the rotational movements may take place through equidistant angular amounts, each in alternating sequence with a displacement of the measuring arrangement along a straight line perpendicular to the central ray of the bundle of X-rays, when a single detector is used as the radiation receiver. Alternatively, it is possible to dispense with the displacements along a straight line path if the radiation receiver is built up of a multiplicity of ray detectors whose signals are simultaneously processed by the measurand converter. For example, the X-ray beam may be fan-shaped and the detectors may be arranged in succession so as to simultaneously receive the X-ray energy after traverse of paths of equal length. A tomographic X-ray apparatus of this kind is described in U.S. Pat. No. 3,974,388 issued Aug. 10, 1976.

SUMMARY OF THE INVENTION

The invention has for its object to extend the utility of a tomographic X-ray apparatus of the rotary scan type.

In accordance with the invention, this object is achieved by virtue of the fact that there are provided means for producing an automatic step by step displacement of the patient support relative to the measuring arrangement in the longitudinal direction during the synchronized pulsing of the scanner and with storage of the signals supplied by the radiation receiver, the measuring arrangement being locked against rotation, and by virtue of the fact that there is connected to the measurand converter a television display unit for reproducing an X-ray shadow image of the patient, which is computed by the measurand converter from the signals of the radiation receiver over the range of longitudinal displacement. In the tomographic X-ray apparatus according to the invention there is provided with the aid of the radiation receiver an X-ray image which is similar to a conventional radiograph.

Other objects, features and advantages of the present invention will become apparent from the following detailed description taken in conjunction with the accompanying sheet of drawings.

DETAILED DESCRIPTION

Figure 1:
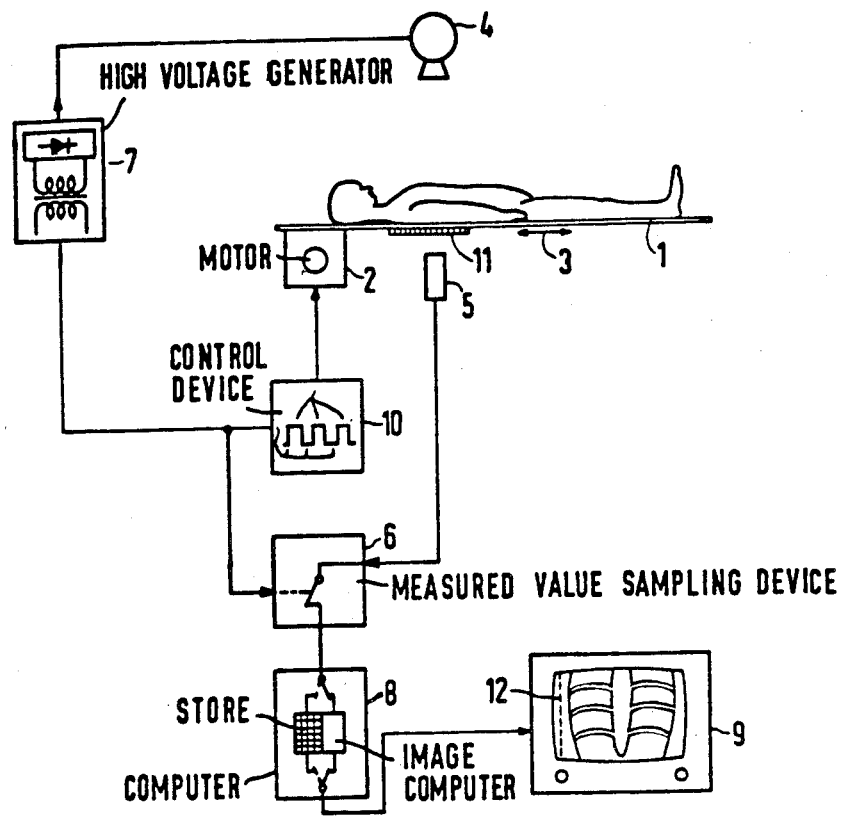
FIG. 1 shows those parts of a tomographic X-ray apparatus according to the invention which constitute the essential apparatus components of the invention and which are utilized in the practice of the inventive method.

In FIG. 1 there is shown a patient's support 1 which is adapted to be subjected to longitudinal reciprocating movement in the direction indicated by double arrow 3 by means of a motor 2. For producing X-ray images, there is provided a measuring arrangement consisting of an X-ray tube 4 and a radiation receiver 5. The output of the radiation receiver 5 is connected to a measurand reading unit 6 so that the analog readings from the radiation receiver 5 can be converted to digital form and stored. The output of the radiation receiver 5 may be sampled by means of the reading unit 6 during intervals corresponding to the intervals of energization of the high voltage generator 7 which supplies the X-ray tube 4. For the sake of diagrammatic illustration, the measured value sampling device 6 is shown as supplying each sample of the readings from the radiation receiver 5 selectively to an image computer component or a "store" component of computer 8. For the case where the measured value sampling device 6 stores the analog readings from receiver 6 in analog form only for the time interval required to convert such analog readings to digital form, during normal tomographic scanning, the digital readings so obtained by means of the sampling device 6 may be supplied to the image computer of component 8 after each energization of the X-ray source 4 for storage in a suitable computer memory. The "store" component for use in producing the longitudinally extensive radiograph may comprise a RAM buffer memory and circulating memory as shown in the tenth figure of an article entitled "The Siretom, a Computerized Transverse Axial Tomograph for Brain Scanning", of which the present applicant is one of the authors, said article being found in the publication *Electromedica*, number 2-3 of 1975, pages 48 through 55. The "store" of component 8 may store each set of readings from receiver 5 corresponding to each patient longitudinal position at a respective row of storage cells so that the rows may be read out in step with the horizontal deflection rate of the television display unit 9.

In addition, FIG. 1 illustrates a control device 10 which controls the longitudinal driving motor 2 and also the measured value sampling device 6 and the high voltage generator 7.

Figure 2:
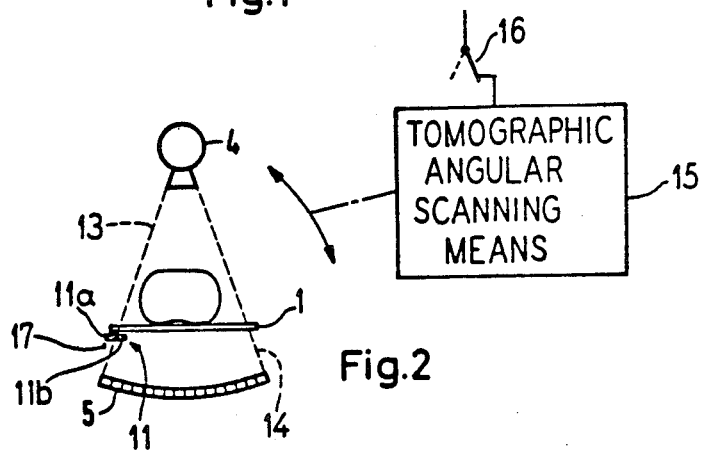
FIG. 2 shows a detail of the tomographic apparatus according to FIG. 1, the view of FIG. 2 being taken in the transverse plane being scanned by the apparatus of FIG. 1.

According to the embodiment of FIG. 2, the measuring arrangement 4, 5 may comprise an X-ray tube 4 which generates a fan-shaped bundle of X-rays having lateral margins as indicated at 13, 14, the X-ray energy being incident upon the radiation receiver 5 which is curved about the focus of the X-ray tube 4. The radiation receiver 5 consists of a detector bank comprising a multiplicity of detector units, for example 242 detectors, so that in the radiation of the patient at a given longitudinal position, 242 individual measurands or readings are obtained. For producing a transverse layer image, the unit 4, 5 is rotated under the control of scanning means 15, FIG. 2, about the patient in a plane perpendicular to the length of the patient support 1 and in the plane of the bundle of rays defined by marginal paths 13, 14 in FIG. 2. The output signals of the radiation receiver 5, which are supplied for each angular position of the measuring arrangement 4, 5, are applied by the measurand-reading unit 6 to the computer 8 which computes therefrom in the known manner a transverse layer image.

In the production of a longitudinally extensive shadowgraph the unit 4, 5 is restricted to a limited angular relationship, such as the particular single angular relationship indicated in FIG. 2, as by opening switch 16 to disable the angular scanning means 15, FIG. 2, and the patient support 1 is shifted with the patient so as to cover the desired longitudinal extent of the patient. During the longitudinal displacement by means of the motor 2, the X-ray tube 4 is pulsed and the radiation receiver 5 is read for each such X-ray pulse. There is therefore obtained for predetermined longitudinal positions of the patient support 1 relative to the measuring arrangement 4, 5 measurands or readings which characterize the attenuation of the X-radiation in its passage through the patient. The "store" of computer 8 stores the successive sets of readings as a basis for generating an X-ray shadow image when the stored values are reproduced on the display unit 9 as is indicated in FIG. 1.

Each set of readings from the receiver 5 for a given longitudinal position of the patient relative to the apparatus 4,5 is utilized to produce an image line extending horizontally on the display unit 9. The number of image dots per image line is equal to the number of detectors in the radiation receiver, so that each horizontal line may have a resolution of 242 dots for the case where there are 242 individual detectors within the receiver 5 as described with respect to FIG. 2. The frequency of the turn-on pulses supplied by control device 10 to the high voltage generator 7 and the speed of operation of motor 2 in driving the support 1 in the direction of arrow 1 are so correlated to one another that the positional resolution in the longitudinal direction corresponds substantially to that which can be provided by the number of detectors in the radiation receiver 5 with respect to the transverse direction. Thus, the control device 10 may supply a turn-on pulse to the high voltage generator at successive longitudinal positions of the patient support 1 relative to the measurement apparatus 4, 5 which are separated by one millimeter, for example.

It is also possible within the scope of the invention to use a single detector as the radiation receiver instead of a bank of detectors if the unit 4, 5 is so arranged as to be transversely displaceable for each relative longitudinal position of the patient to the unit 4, 5. Where a single detector is utilized for the receiver 5, the readings from the detector for the successive transverse positions would be stored as a set of readings, for example each reading being converted to digital form prior to storage. The successive sets of readings so stored would then represent information with respect to successive longitudinal portions of the patient as in the example using the arrangement of FIG. 2 and would be displayed exactly as shown in FIG. 1.

In the embodiment described with reference to FIG. 2, the pulsing of the X-ray tube 4 takes place with the patient's support 1 in predetermined longitudinal positions, that is to say the successive turn-on pulses are supplied to the X-ray generator 7 from the control device 10 at predetermined longitudinal positions of the patient's support 1.

It is also conceivable within the scope of the invention for the support 1 to be fixedly located and for the measuring arrangement 4, 5 to be arranged to be displaced in the longitudinal direction of the support 1 both for producing a synoptic radiographic picture and for the subsequent selection of a specific longitudinal position relative to the patient for scanning to produce a transverse layer or tomographic image.

The computer 8 comprises a store which stores the signals corresponding to an image line which signals are supplied to the store from the radiation receiver 5 via the measured value sampling device 6. The store may have a series of storage locations for the set of readings corresponding to each longitudinal position of the patient, and the number of such series of storage locations may then correspond to the number of detectors of radiation receiver 5, FIG. 2. Thus, after the successive sets of readings are stored by means of the store component of computer 8, the desired synoptic image can be reproduced on the television display unit 9.

For the reproduction of a synoptic exposure from the store component of computer 8, no actual image computation takes place so that the image computer component of computer 8 is not utilized during the generation of the longitudinally extensive radiographic image. The computer store of component 8 for purposes of generating the radiographic image has a number of image stores which is equal to the number of image lines times the number of image dots per image line. For the example of FIG. 2, as previously mentioned, each image line store may comprise 242 storage cells. For reproducing a synoptic exposure, there takes place at the commencement of the displacement of the support 1 by means of the motor 2 a change-over of the computer input, that is to say a disconnection of the image computer component of computer 8 and a connection of the computer input to the described store component of computer 8. In this case, the display unit 9 is also disconnected from the image computer component of computer 8 and connected to said store component at its input for displaying the radiographic or synoptic image as specifically illustrated in FIG. 1.

The control device 10 is so constructed that it turns on the motor 2 and the X-ray generator 7 pulse-wise. Therefore, the support motor 2 is first turned on or pulsed for carrying out a displacement step of the support 1. For this purpose, the motor 2 may be a conventional stepping motor which indexes a desired longitudinal increment for each pulse supplied thereto. After completion of this longitudinal displacement step, the X-ray tube 4 is turned on by means of the control device 10 supplying a turn-on pulse to the X-ray generator 7 so as to produce an X-ray pulse of desired duration. The support motor 2 then receives a further turn-on pulse for carrying out a further displacement step of the support 1; thereafter, the X-ray tube 4 is turned on by way of the X-ray generator, and so on. The control device 4, 5 measurands or readings which characterize the attenuation of the X-radiation in its passage through the patient. The "store" of computer 8 stores the successive sets of readings as a basis for generating an X-ray shadow image when the stored values are reproduced on the display unit 9 as is indicated in FIG. 1.

Each set of readings from the receiver 5 for a given longitudinal position of the patient relative to the apparatus 4, 5 is utilized to produce an image line extending horizontally on the display unit 9. The number of image dots per image line is equal to the number of detectors in the radiation receiver, so that each horizontal line may have a resolution of 242 dots for the case where there are 242 individual detectors within the receiver 5 as described with respect to FIG. 2. The frequency of the turn-on pulses supplied by control device 10 to the high voltage generator 6 and the speed of operation of motor 2 in driving the support 1 in the direction of arrow 1 are so correlated to one another that the position resolution in the longitudinal direction corresponds substantially to that which can be provided by the number of detectors in the radiation receiver 5 with respect to the transverse direction. Thus, the control device 10 may supply a turn-on pulse to the high voltage generator at successive longitudinal positions of the patient support 1 relative to the measurement apparatus 4, 5 which are separated by one millimeter, for example. A scale 11, FIG. 2, with suitable scale divisions may be detachably secured at any selected position along the length of support 1 for movement therewith. By way of example, the scale 11 is shown with a section 11a outside the beam path 13, 14 and a section 11b just within a margin 13 of the X-ray energy impinging on the detectors of receiver 5. By storing the readings from the detectors aligned with the scale 11 and storing such readings for each successive longitudinal position, the scale 11 is simultaneously produced in the television image as a marking means 12, FIG. 1. This enables the patient to be readily positioned longitudinally in relation to the measuring arrangement 4, 5. With the aid of the television image, it is possible to identify a particular desired point of the scale 11 and to position this point relative to a fixed reference mark 17 cooperating with the section 11a of scale 11 which has the illustrated visible divisions aligned with those of section 11b which produce the divisions of marking means 12. Thereafter, a transverse layer tomographic image of the chosen region may be formed in the conventional manner.

In carrying out the method of the present invention with a semiconductor X-ray detector of the type illustrated in FIG. 2, the scale 11 is fixed to the patient support 1 along the longitudinal extent of the patient within which the scanning layer is to be located. The support 1 with the patient thereon then is placed in an initial position, with the X-ray beam path 13, 14 arranged to impinge at one longitudinal end of the scale 11 and the motor 2 set to index the support 1 so as to progressively move the scale 11 together with the patient through the scanning region. The measured value sampling device 6 is placed in the operating mode such that the switch of component 6 is normally opened but is closed for a suitable interval in response to each pulse from the control device 10. Similarly, the computer component 8 is switched over so that the computer input is connected with the store of component 8 utilized to provide storage for the successive sets of readings from receiver 5. The control device 10 is now turned on and proceeds to alternately supply control pulses to the generator component 7 and sampling device 6 on the one hand, and to the stepping motor 2 on the other hand. Thus, during each energization of the X-ray source 4, a suitable sample of the readings from the detectors of receiver 5 is stored within the store component of computer 8, whereupon the motor 2 is energized to produce a longitudinal indexing movement, the sampling device 6 and generator 7 then again being pulsed, and so on. When the successive sets of readings from receiver 5 have been stored in this way, the stored values can be processed as described in detail in the aforementioned *Electromedica* article, but in such a manner that each set of stored readings is scanned in synchronism with the line rate of the display device 9 so that each set of readings appears as a horizontal line on the display screen as is illustrated in FIG. 1. The visual scale section 11a may have fine divisions corresponding to the vertical resolution of the image to be displayed, for example 242 divisions with a spacing corresponding to the horizontal resolution afforded by the detector units of the receiver 5 of FIG. 2, while scale 11b may have somewhat coarser divisions only, so as to be readily discriminated when displayed at 12 on the display screen. In this way, the patient can be conveniently positioned with an accuracy generally corresponding to the longitudinal resolution of the tomographic scanning system.

Further Supplementary Discussion

A commercial system in accordance with the present invention is described in an issue of *C. T. NEWS* (in English) dated Aug. 1980, eight pages, and identified by Order No. M-R36/1878.101, said brochure having been published by the manufacturer Siemens Aktiengesellschaft. The content of this brochure entitled "Topogram, Survey view in the mRrange" is incorporated herein by reference in its entirety.

A report of a further use of the commercial system is reported in an article in *Electromedica* published by Siemens Aktiengesellschaft, the article by Rienmüller et al. being entitled "The Topogram in Mediastinal Computerized Tomography", and being found in Number 2/1981 of the English Edition at pages 117–121. This article is incorporated herein by reference.

Further developments in the commercial system are described in a brochure *Data,* Edition in English, of Siemens AG entitled "Topogram DR2 and DR3 SIC C 132" consisting of four pages, Order No. M-R 36/7386-101 3, and in an issue of *C T NEWS* of Siemens AG (in English), entitled "SOMATOM DR: New options, new evaluations and new scan modes with the software version C," Order No. M-R 36/1926-101 WS 06 83 3, and these two technical disclosures are also incorporated herein by reference.

I claim as my invention:

1. Tomographic apparatus for the production of transverse-layer images of a patient, comprising
    (a) a patient support having a longitudinal direction,
    (b) an X-ray measuring arrangement including an X-ray source which produces a beam of X-ray energy for penetrating a patient transverse layer, and radiation measurement means arranged in a common transverse plane with said X-ray source, and receiving the X-ray energy of the beam after transmission through a patient transverse layer lying in said common transverse plane so as to provide an output comprising a set of individual measurement signals as a measure of the radiation 10 thus comprises a simple sequence timer circuit which alternately supplies control pulses to motor 2 and to high voltage generator 7 during the storage of the successive sets of readings from the receiver 5.

The measurand-reading unit 6 is shown as including a switch which connects the output of the radiation receiver 5 to the input of the computer 8 each time it receives at its left-hand input a pulse from the control device 10 signifying that the X-ray tube 4 has been turned on. Thus, a sample of suitable duration of the output from the radiation receiver 5 for each detector shown in FIG. 2, for example, is transmitted to the store of component 8. Of course, the switch of component 6 is of an electronic nature. If the store of component 8 is a digital storage, then component 6 may include a suitable analog accumulator for the respective readings from the detectors and suitable analog to digital circuitry for converting the readings to digital form and supplying them to the store of component 8.

Supplementary Discussion

Simply for the sake of example, the radiation receiver 5 may comprise a row of semiconductor diodes presenting respective generally narrow rectangular edge faces to the impinging radiation, a fluorescent layer being interposed or sandwiched between every two diodes and at the opposite ends of the row of diodes. In such a radiation receiver, the X-radiation strikes the fluorescent layers at the relatively narrow generally rectangular edges thereof and causing each fluorescent layer to emit visible light in one or both lateral directions such that the impinging radiation produces a corresponding current flow in the respective associated semiconductor diodes. A semiconductor X-ray detector of this type is disclosed in German patent application No. P 26 22 655.1 filed May 20, 1976 wherein the inventors are the present applicant, Dr. Gunter Luderer and Burghard Weinkauf, such case being identified by the assignee reference number VPA 76 P 5058.

In carrying out the method of the present invention with a semiconductor X-ray detector of the type illustrated in FIG. 2, the support 1 with the patient thereon is placed in an initial position, with the X-ray beam path 13, 14 arranged to impinge at one longitudinal position and the motor 2 set to index the support 1 so as to progressively move the patient support 1 through the scanning region. The measured value sampling device 6 is placed in the operating mode such that the switch of component 6 is normally opened but is closed for a suitable interval in response to each pulse from the control device 10. Similarly, the computer component 8 is switched over so that the computer input is connected with the store of component 8 utilized to provide storage for the successive sets of readings from receiver 5. The control device 10 is now turned on and proceeds to alternately supply control pulses to the generator component 7 and sampling device 6 on the one hand, and to the stepping motor 2 on the other hand. Thus, during each energization of the X-ray source 4, a suitable sample of the readings from the detectors of receiver 5 is stored within the store component of computer 8, whereupon the motor 2 is energized to produce a longitudinal indexing movement, the sampling device 6 and generator 7 then again being pulsed, and so on. When the successive sets of readings from receiver 5 have been stored in this way, the stored values can be processed as described in detail in the aforementioned *Electromedica* article, but in such a manner that each set of stored readings is scanned in synchronism with the line rate of the display device 9 so that each set of readings appears as a horizontal line on the display screen as is illustrated in FIG. 1.

It will be apparent that many modifications and variations may be effected without departing from the scope of the novel concepts and teachings of the present invention.

Disclosure from Liebetruth U.S. Pat. No. 4,174,481

A tomographic X-ray apparatus is described in U.S. Pat. No. 3,974,388 issued Aug. 10, 1976. The cited patent represents a tomographic apparatus seeking to facilitate the desired exact positioning of the patient wherein markings are applied relative to a precisely determined patient location such as the eye-ear line. In this apparatus, for example, an adhesive band may be adhered to the side of the patient's head, having a scale disposed longitudinally of the patient which is utilized in conjunction with a light visor to enable a precise determination of the position of the scanning layer relative to the reference line.

The invention has for its object to design a tomographic X-ray apparatus of the kind mentioned such that an exact positioning of the patient in relation to the measuring arrangement can be readily effected.

In accordance with the invention, this object is achieved by virtue of the fact that there are provided means for producing a relative displacement between the measuring arrangement and the patient's support in the longitudinal direction of the latter during the processing of the signals supplied by the radiation receiver, the measuring arrangement being locked against rotation, and by virtue of the fact that there is connected to the measurand converter a television display unit for reproducing the X-ray shadow image of the patient, which is computed by the measurand converter from the signals of the radiation receiver over the range of longitudinal displacement. In the tomographic X-ray apparatus according to the invention there is provided with the aid of the radiation receiver an X-ray image which is similar to a conventional radiograph. This X-ray image which is reproduced on the television display unit makes it possible to select with accuracy the desired transverse layer which is to be measured by means of the tomographic measuring arrangement. Simple positioning of the patient in relation to the measuring arrangement is possible if there is mounted on the patient's support a scale which is reproduced on the television display unit together with the X-ray shadow image.

For the exact positioning of the patient longitudinally in relation to the measuring arrangement 4, 5 there is provided on the patient support 1 a scale 11 having divisions which can be reproduced by X-rays. Before the actual production of a transverse layer image, the unit 4, 5 is restricted to a limited angular relationship, such as the particular single angular relationship indicated in FIG. 2, as by opening switch 16 to disable the angular scanning means 15, FIG. 2, and the patient support 1 is shifted with the patient so as to cover the longitudinal extent of the patient which includes the particular transverse layer to be located. During the longitudinal displacement by means of the motor 2, the X-ray tube 4 is pulsed and the radiation receiver 5 is read for each such X-ray pulse. There is therefore obtained for predetermined longitudinal positions of the patient support 1 relative to the measuring arrangement intensity of the transmitted beam over the transverse extent of the patient transverse layer, (c) tomographic angular scanning means coupled with the X-ray source operable in a tomographic angular scanning mode for producing rotational movements of said X-ray source in said common transverse plane through a wide range of angular relationships relative to said patient transverse layer so as to generate a sufficient number of sets of individual measurement signals to define a tomographic layer image of the patient transverse layer, (d) longitudinal drive means operating in a shadow image generating mode for producing relative longitudinal movement between the measuring arrangement and the patient support in the longitudinal direction of the latter, (e) control means operating in said shadow image generating mode during relative longitudinal movement of said patient support through successive longitudinal positions and controlling said X-ray source, (f) computer means operating in the shadow image generating mode for the storage of an X-ray shadow image of the patient having a substantial transverse extent and having a longitudinal extent corresponding to the range of longitudinal movement produced by said longitudinal drive means during operation in said shadow image generating mode, and operating in said tomographic angular scanning mode for computing a tomographic layer image of the patient transverse layer based on the sets of individual measurement signals generated during operation of said tomographic angular scanning means, (g) measured value sampling means responsive to said control means and operable in said shadow image generating mode for effecting ony one sampling of the output from said radiation measurement means for each of said successive longitudinal positions and for supplying respective sets of shadow image measurement signals based on the respective samplings of the output of said radiation measurement means, to said computer means for storage thereby, and (h) video display means connectable with said computer means and operating in a shadow image display mode for displaying the respective sets of shadow image measurement signals as successive lines of a video image, (i) said control means operating in said shadow image generating mode to intermittently turn on the beam of X-ray energy from said X-ray source with the frequency of the turning on of said beam being correlated with the rate of operation of said longitudinal drive means such that only an X-ray shadow image is generated during said shadow image mode with the patient being scanned by the beam of X-ray energy from only a single angular relationship relative to the patient support.

2. Tomographic apparatus for the production of transverse-layer images of a patient, comprising
(a) a patient support having a longitudinal direction,
(b) an X-ray measuring arrangement including an X-ray source which produces a beam of X-ray energy for penetrating a patient transverse layer at a transverse plane, and radiation measurement means arranged to receive the X-ray energy of the beam after transmission through the patient transverse layer so that the radiation measurement means provides a set of measurement readings which are measures of the radiation intensity of the transmitted beam over the transverse extent of the patient transverse layer, (c) tomographic angular scanning means coupled with the X-ray source and operable in a tomographic angular scanning mode for producing rotational movements of the X-ray source in said transverse plane through a wide range of angular relationships relative to the patient transverse layer so as to generate a sufficient number of sets of measurement readings to define a tomographic layer image of the patient transverse layer, (d) longitudinal drive means operable in a shadow image generating mode for producing longitudinal movement of the patient support in the longitudinal direction of the latter, (e) control means operating in said shadow image generating mode for producing successive pulses of X-ray energy from said X-ray source during longitudinal movement of said patient support through successive longitudinal positions while the measuring arrangement is in a single angular relationship to said patient support, and (f) shadow image storage means operating in said shadow image generating mode for the storage of a set of measurement readings from the radiation measurement means in each of the successive longitudinal positions of said patient support for defining an X-ray shadow image of the patient having a substantial transverse extent and having a longitudinal extent corresponding to the range of longitudinal movement produced by said longitudinal drive means during operation in said shadow image generating mode, and (g) measured value processing means controlled by said control means and operating in said shadow image generating mode for transmitting only the readings defining said X-ray shadow image to said shadow image storage means, (h) said control means operating in said shadow image generating mode for producing a pulse of X-ray energy from said X-ray source and for actuating said measured value processing means to transmit the set of measurement readings from the radiation receiver produced by such pulse to said shadow image storage means, for each of the successive longitudinal positions of the patient support, said control means producing the pulses of X-ray energy with a frequency correlated with the rate of longitudinal movement of said patient support during said shadow image generating mode so as to provide a predetermined positional resolution in said longitudinal direction.

3. Tomographic apparatus according to claim 2, with said radiation measurement means providing a predetermined transverse image resolution, and said control means producing pulses of X-ray energy during operation in said shadowgraphic mode such as to provide a predetermined positional resolution in said longitudinal direction substantially corresponding to the predetermined transverse image resolution provided by said radiation measurement means.

4. Tomographic apparatus according to claim 3, with said control means automatically correlating the frequency of the successive pulses of X-ray energy with the rate of longitudinal movement of said patient support so as to provide said predetermined positional resolution in said longitudinal direction.

5. Tomographic apparatus for the production of transverse-layer images of an exposed subject, comprising a patient's support, an X-ray measuring arrangement, including an X-ray source which produces a beam of X-ray energy for penetrating the exposed subject with respect to a transverse plane, and a radiation receiver which provides readings which are measures of the radiation intensity of the transmitted beam, scanning means coupled with the source for producing rotational movements through a wide range of angular relationships so as to generate a sufficient number of sets of readings to define a tomographic layer image, longitudinal drive means for producing relative longitudinal movement between the measuring arrangement and the patient's support in the longitudinal direction of the latter during storage of the readings from the radiation receiver, control means coupled with the longitudinal drive means and operable in an automatic shadow image generating mode for automatically producing longitudinal movement of said patient support through successive longitudinal positions while the measuring arrangement is locked in a single angular relationship, shadow image storage means operable for the storage of only one set of readings from the radiation receiver in each of the successive positions of said patient support for defining an X-ray shadow image of the patient having a substantial transverse extent and having a longitudinal extent corresponding to the range of longitudinal movement produced by said longitudinal drive means during automatic operation of said control means in said automatic shadow image generating mode, said shadow image storage means having sequentially accessible sets of storage positions each for storing only one set of readings from said radiation receiver, and means responsive to said control means and automatically operable in said automatic shadow image generating mode for transmitting only one set of readings from said radiation receiver to said sequentially accessible sets of storage positions of said shadow image storage means for each of said successive longitudinal positions, and for storing at the respective sequentially accessible sets of storage positions the respective sets of readings taken in the successive longitudinal positions, such that sequential read out of said sets of sequentially accessible storage positions generates an X-ray shadow image of the patient over said longitudinal extent of the successive longitudinal positions.

6. Tomographic apparatus for the production of transverse-layer images of a patient, comprising (a) a patient support having a longitudinal direction, (b) an X-ray measuring arrangement including an X-ray source which produces a fan-shaped beam of X-ray energy for penetrating a patient transverse layer at a transverse plane, and a radiation receiver in said transverse plane which provides readings which are measures of the radiation intensity of the transmitted fan-shaped beam, (c) scanning means coupled with the X-ray source for producing rotational movements of said fan-shaped beam in said transverse plane through a wide range of angular relationships relative to the patient transverse layer so as to generate a sufficient number of sets of readings to define a tomographic layer image of the patient transverse layer, (d) longitudinal drive means operable in a shadow image generating mode for producing relative longitudinal movement between the measuring arrangement and the patient support in the longitudinal direction of the latter during storage of the readings from the radiation receiver, (e) control means coupled with the longitudinal drive means and operable in said shadow image generating mode for supplying turn-on pulses for intermittently turning on said X-ray source such that the X-ray source is pulsed during the relative longitudinal movement of said patient support through successive longitudinal positions while the X-ray source is locked in a single angular relationship, and (f) shadow image storage means operable in said shadow image generating mode for the storage of only one set of readings from the radiation receiver in each of the successive longitudinal positions for defining an X-ray shadow image of the patient having a substantial transverse extent and having a longitudinal extent corresponding to the range of relative longitudinal movement produced by said longitudinal drive means during operation of said control means in said shadow image generating mode, (g) said control means comprising sequence timer means operable in said shadow image generating mode for correlating the frequency of the turn-on pulses supplied to effect the intermittent turning on of the X-ray source with the speed of operation of the longitudinal drive means in producing said relative longitudinal movement while the X-ray source is locked in said single angular relationship such that said X-ray source is pulsed only at said successive longitudinal positions which define said X-ray shadow image of the patient and such that said X-ray energy penetrates each successive patient region at the transverse plane with only a single angular relationship to such patient region at each of said successive longitudinal positions during the operation of said sequence timer means in said shadow image generator mode.

7. Tomographic apparatus according to claim 6, with said sequence timer means supplying said turn-on pulses during operation in said shadow image generating mode with a frequency so correlated with said speed of operation of said longitudinal drive means that the X-ray source is pulsed only at successive longitudinal positions which are separated by one millimeter.

8. Tomographic apparatus according to claim 6 with said radiation receiver comprising a bank of detectors which are successively offset from each other in a transverse direction for receiving said fan-shaped beam of X-ray energy from said X-ray source, the number of successively offset detectors of said bank providing a transverse image resolution in the transverse direction, said sequence timer means supplying said turn-on pulses during operation in said shadow image generating mode with a frequency so correlated with said speed of operation of said longitudinal drive means that the X-ray source is pulsed only at successive longitudinal positions which are separated by a longitudinal increment substantially corresponding to said transverse image resolution given by said number of successively offset detectors of said bank.

9. Tomographic apparatus according to claim 6, with said longitudinal drive means comprising stepping motor means which indexes a desired longitudinal increment for each control pulse supplied thereto, said sequence timer means during operation in said shadow image generating mode supplying only one turn-on pulse for turning on said X-ray source to emit one pulse of X-ray energy between the successive indexing movements of said stepping motor means and operating such that after indexing of the stepping motor means to each of said successive longitudinal positions, the X-ray source is turned on by said sequence timer means so as to produce only one X-ray pulse of duration to produce one shadow image exposure, said sequence timer means alternately supplying said turn-on pulses and the control pulses during the storage of the successive sets of readings from said radiation receiver so as to define said X-ray shadow image while throughout the shadow image generating mode the X-ray source remains locked in said single angular relationship.

10. Tomographic apparatus for the production of transverse-layer images of a patient, comprising
(a) a patient support having a longitudinal direction,
(b) an X-ray measuring arrangement including an X-ray source which produces a beam of X-ray energy for penetrating a patient transverse layer at a transverse plane, and a radiation receiver in said transverse plane arranged to receive the X-ray energy of the beam after transmission through the patient transverse layer so that the radiation receiver provides readings which are measures of the radiation intensity of the transmitted beam,
(c) tomographic angular scanning means coupled with the X-ray source and operable in a tomographic angular scanning mode for producing rotational movements of the X-ray source in said transverse plane through a wide range of angular relationships relative to the patient transverse layer so as to generate a sufficient number of sets of readings to define a tomographic layer image of the patient transverse layer,
(d) longitudinal drive means operable in a shadow image generating mode for producing longitudinal movement of the patient support in the longitudinal direction of the latter,
(e) control means coupled with the longitudinal drive means and operable in said shadow image generating mode for producing successive pulses of X-ray energy from said X-ray source during longitudinal movement of said patient support through successive longitudinal positions while the measuring arrangement is locked in a single angular relationship such that the successive pulses of X-ray energy produce successive X-ray beams in the transverse plane and impinging on the radiation receiver which successive X-ray beams in said transverse plane have only a single angular relationship to a patient on the patient support,
(f) shadow image storage means operable in said shadow image generating mode for the storage of the readings from the radiation receiver in each of the successive longitudinal positions of said patient support for defining an X-ray shadow image of the patient having a substantial transverse extent and having a longitudinal extent corresponding to the range of longitudinal movement produced by said longitudinal drive means during operation of said control means in said shadow image generating mode, and
(g) measured value processing means responsive to said control means and operable in said shadow image generating mode for transmitting only the readings defining said X-ray shadow image to said shadow image storage means,
(h) said control means comprising sequencing means operable in said shadow image generating mode for producing a pulse of X-ray energy from said X-ray source and for actuating said measured value processing means to transmit the readings from the radiation receiver produced by such pulse to said shadow image storage means, for each of the successive longitudinal positions of the patient support, said sequencing means producing the pulses of X-ray energy with a frequency correlated with the speed of operation of said longitudinal drive means during said shadow image generating mode so as to provide a predetermined positional resolution in said longitudinal direction.

11. Tomographic apparatus according to claim 10, with said radiation receiver providing a predetermined transverse image resolution, and said sequencing means producing pulses of X-ray energy during operation in said shadowgraphic mode such as to provide a predetermined positional resolution in said longitudinal direction substantially corresponding to the predetermined transverse image resolution provided by said radiation receiver.

12. Tomographic apparatus according to claim 10, with said measured value processing means being responsive to a pulse from said sequencing means to transmit a sample of suitable duration of the output of the radiation receiver to said shadow image storage means, and said sequencing means transmitting only one pulse to said measured value processing means for each of the successive longitudinal positions of said patient support during operation in said shadow image generating mode.

13. Tomographic apparatus according to claim 10, with computer means operable in said tomographic angular scanning mode for storing the sets of readings defining a tomographic layer image of the patient transverse layer, and operable in said shadow image generating mode to provide for the storage of only the readings for defining an X-ray shadow image, and switch means for switching the computer means between said tomographic angular scanning mode and said shadow image generating mode.

14. Tomographic apparatus for the production of transverse-layer images of a patient, comprising
(a) a patient support having a longitudinal direction,
(b) an X-ray measuring arrangement including an X-ray source which produces a beam of X-ray energy for penetrating a patient transverse layer, and a radiation receiver arranged in a common transverse plane with said X-ray source, and receiving the X-ray energy of the beam after transmission through a patient transverse layer lying in said common transverse plane so as to provide an output which is a measure of the radiation intensity of the transmitted beam, (c) tomographic angular scanning means coupled with the X-ray source and operable in a tomographic angular scanning mode for producing rotational movements of said X-ray source in said common transverse plane through a wide range of angular relationships relative to said patient transverse layer so as to generate a sufficient number of sets of readings to define a tomographic layer image of the patient transverse layer, (d) longitudinal drive means operable in a shadow image generating mode for producing relative longitudinal movement between the measuring arrangement and the patient support in the longitudinal direction of the latter, (e) control means coupled with the longitudinal drive means and operable in said shadow image generating mode for producing relative longitudinal movement of said patient support through successive longitudinal positions while the measuring arrangement is locked in a single angular relationship, (f) computer means operable in the shadow image generating mode for the storage of an X-ray shadow image of the patient having a substantial transverse extent and having a longitudinal extent corresponding to the range of longitudinal movement produced by said longitudinal drive means during operation of said control means in said shadow image generating mode, and operable in said tomographic angular scanning mode for computing a tomographic layer image of the patient transverse layer based on the sets of readings generated during operation of said tomographic angular scanning means, (g) measured value sampling means responsive to said control means and operable in said automatic shadow image generating mode for effecting only one sampling of the output from said radiation receiver for each of said successive longitudinal positions and for supplying respective sets of shadow image readings based on the respective samplings of the output of said radiation receiver to said computer means for storage thereby, (h) video display means connectable with said computer means and operable in a shadow image display mode for displaying the respective sets of shadow image readings as successive lines of a video image, and operable in a tomographic layer image display mode for displaying a computed tomographic layer image, (i) said control means being turned on for the duration of said shadow image generating mode and being operable throughout the duration of said shadow image generating mode to supply turn-on pulses to intermittently turn on the X-ray beam from said X-ray source with the frequency of said turn-on pulses being correlated with the speed of operation of said longitudinal drive means such that only an X-ray shadow image is generated during said shadow image mode with the patient being scanned by the X-ray source from only a single angular relationship relative to the patient, and (j) switch means connected with said computer means and with said video display means and operable in one switching condition to supply the respective sets of shadow image readings from the computer means to said video display means for display of the X-ray shadow image,—and operable in a second switching condition to supply the computed tomographic layer image from the computer means to said video display means for display thereby.

15. Tomographic apparatus for the production of transverse-layer images of a patient, comprising (a) a patient support having a longitudinal direction, (b) an X-ray measuring arrangement including X-ray source means which produces a fan-shaped beam of X-ray energy having a lateral extent for penetrating a patient transverse layer at a transverse plane, and radiation measurement means receiving said fan-shaped beam and providing a set of a given number of respective individual measurements of radiation intensity of respective portions of the fan-shaped beam after transmission along respective laterally offset paths through the patient transverse layer, (c) angular scanning means coupled with the X-ray source means and operating in a tomographic angular scanning mode for producing rotational movement of said fan-shaped beam in said transverse plane through a wide range of angular relationships relative to the patient transverse layer so as to generate a sufficient number of sets of said individual measurements to define a tomographic layer image of the patient transverse layer, (d) computer means connected with said radiation measurement means and operating in said tomographic angular scanning mode for the computation of a transverse-layer image based on said sets of said individual measurements, (e) longitudinal scanning means operating in a shadow image generating mode for producing longitudinal movement of the patient support relative to the fan-shaped beam of X-ray energy in the longitudinal direction of the patient support and effecting the production of successive sets of said individual measurements from the radiation measurement means in successive relative longitudinal positions of the patient support while the measuring arrangement is locked in a single angular relationship, and supplying the successive sets of individual measurements to said computer means for the generation of an X-ray shadow image of the patient having a longitudinal extent corresponding to the extent of relative longitudinal movement of the patient support produced during said shadow image generating mode, and having a transverse extent corresponding to the lateral extent of said fan-shaped beam, (f) said longitudinal scanning means in said shadow image generating mode matching the rate of said relative longitudinal movement of said patient support and the frequency of the production of said successive sets of individual measurements from the radiation measurement means to obtain a predetermined resolution of said X-ray shadow image in the longitudinal direction generally corresponding with the image resolution which is given by said number of individual measurements produced by said radiation measurement means.

16. Tomographic apparatus according to claim 15, wherein the X-ray measuring arrangement is longitudinally and rotationally fixedly located during said shadow image generating mode, and the patient support is longitudinally driven by means of said longitudinal scanning means.

17. Tomographic apparatus according to claim 15, with an image display means for visually reproducing an X-ray shadow image of the patient based on the successive sets of individual measurements produced in said shadow image generating mode.

18. Tomographic apparatus according to claim 15, with said radiation measurement means producing said number of respective individual measurements in each of the successive relative longitudinal positions of the patient support during said shadow image generating mode, and said number of individual measurements being at least two hundred and forty-two.

19. Tomographic apparatus according to claim 15, with said patient support having location measurement means for identifying the longitudinal position of the patient support relative to said X-ray measurement arrangement, image display means coupled with said computer means for visually reproducing an X-ray shadow image of the patient based on the successive sets of individual measurements produced in said shadow image generating mode and for visually displaying, along with the X-ray shadow image, means for identifying the respective longitudinal positions of respective segments of the displayed X-ray shadow image in relation to said X-ray measurement arrangement.

20. Tomographic apparatus according to claim 15, wherein the radiation measurement means is comprised of a bank of respective detectors for receiving the respective portions of the fan-shaped beam, said longitudinal scanning means during said shadow image generating mode turning on the X-ray source means only when the measuring arrangement and the patient support are in successive relative longitudinal positions which are successively offset longitudinally by a longitudinal increment substantially corresponding to the image resolution given by the number of detectors of said bank.

21. Tomographic apparatus according to claim 20, with said bank of detectors comprising at least two hundred and forty-two detectors arranged for receiving respective portions of the fan-shaped beam.

22. Tomographic apparatus for the production of transverse-layer images of a patient comprising
(a) a patient support having a longitudinal direction,
(b) an X-ray measuring arrangement including X-ray source means which produces a fan-shaped beam of X-ray energy having transverse extent for penetrating a patient transverse layer at a transverse plane, and radiation measurement means receiving said fan-shaped beam and providing a set of respective individual measurement readings representing radiation intensity of respective transversely offset portions of the fan-shaped beam after transmission along respective transversely offset paths through the patient transverse layer,
(c) angular scanning means coupled with the X-ray source means and operating in a tomographic angular scanning mode for producing rotational movement of said fan-shaped beam in said transverse plane through a wide range of angular relationships relative to the patient transverse layer so as to generate a sufficient number of sets of said individual measurement readings to define a tomographic layer image of the patient transverse layer,
(d) computer means connected with said radiation measurement means and operating in said tomographic angular scanning mode for the computation of a transverse-layer image based on said sets of said individual measurement readings, and
(e) longitudinal scanning means operating in an automatic shadow image generating mode for producing longitudinal movement of the patient support relative to the fan-shaped beam of X-ray energy in the longitudinal direction of the patient support and automatically effecting the production of successive sets of said individual measurement readings from the radiation measurement means in successive relative longitudinal positions of the patient support while the measuring arrangement is locked in a single angular relationship, and supplying the successive sets of individual measurement readings to said computer means for the generation of an X-ray shadow image of the patient having a longitudinal extent corresponding to the extent of relative longitudinal movement of the patient support produced during said automatic shadow image generating mode, and having a transverse extent corresponding to the transverse extent of said fan-shaped beam.

23. Tomographic apparatus according to claim 22, wherein the X-ray measuring arrangement is longitudinally and rotationally fixedly located during said automatic shadow image generating mode, and the patient support is longitudinally driven by means of said longitudinal scanning means.

24. Tomographic apparatus according to claim 22, with an image display means connectable with said computer means for visually reproducing an X-ray shadow image of the patient based on the successive sets of individual measurement readings produced in said automatic shadow image generating mode.

25. Tomographic apparatus according to claim 22, with said radiation measurement means producing a given number of respective individual measurement readings in each of the successive relative longitudinal positions of the patient support during said automatic shadow image generating mode, and said number of individual measurement readings being at least two hundred and forty-two.

26. Tomographic apparatus according to claim 22, with said patient support having location measurement means for identifying the longitudinal position of the patient support relative to said X-ray measurement arrangement, image display means coupled with said computer means for visually reproducing an X-ray shadow image of the patient based on the successive sets of individual measurement readings produced in said automatic shadow image generating mode and for visually displaying, along with the X-ray shadow image, means for identifying the respective longitudinal positions of respective segments of the displayed X-ray shadow image in relation to said X-ray measurement arrangement.

27. Tomographic apparatus according to claim 22, wherein the radiation measurement means is comprised of a bank of respective detectors for receiving the respective transversely offset portions of the fan-shaped beam, said longitudinal scanning means during said automatic image generating mode turning on the X-ray source means only when the measuring arrangement and patient support are in successive relative longitudinal positions which are successively offset longitudinally by a longitudinal increment substantially corresponding to the image resolution given by the number of detectors of said bank.

28. Tomographic apparatus according to claim 27, with said bank of detectors comprising at least two hundred and forty-two detectors arranged for receiving respective transversely offset portions of the fan-shaped beam.

29. Tomographic apparatus for the production of transverse-layer images of a patient, comprising
   (a) a patient support having a longitudinal direction,
   (b) an X-ray measuring arrangement including an X-ray source which produces a beam of X-ray energy for penetrating a patient transverse layer lying in a transverse plane, and radiation measurement means which provides a set of measurement readings which are measures of the radiation intensity of the transmitted beam over the transverse extent of the patient transverse layer,
   (c) angular scanning means coupled with the X-ray source for producing rotational movements of the beam of X-ray energy through a wide range of angular relationships to the patient transverse layer so as to generate a sufficient number of sets of measurement readings to define a tomographic layer image,
   (d) longitudinal scanning means producing longitudinal movement of the patient support relative to said beam of X-ray energy and producing measurement readings from the radiation measurement means in successive longitudinal positions of said patient support relative to said beam of X-ray energy in an automatic shadow image generating mode while the beam is in a single angular relationship with respect to the patient support, and
   (e) shadow image storage means operating during said automatic shadow image generating mode for the storage of a set of measurement readings from the radiation measurement means in each of the successive longitudinal positions of said patient support relative to said beam of X-ray energy for defining an X-ray shadow image of the patient having a substantial transverse extent and having a longitudinal extent corresponding to the range of longitudinal movement produced by said longitudinal scanning means during said automatic shadow image generating mode.

30. Tomographic apparatus according to claim 29, wherein the beam of X-ray energy is longitudinally and rotationally fixedly located during said automatic shadow image generating mode, and the patient support is longitudinally driven by means of said longitudinal scanning means.

31. Tomographic apparatus according to claim 29, with an image display means connectable with said shadow image storage means for visually reproducing an X-ray shadow image of the patient based on the successive sets of measurement readings produced in said automatic shadow image generating mode.

32. Tomographic apparatus according to claim 29, with said radiation measurement means producing a given number of respective individual measurement readings in each of the successive relative longitudinal positions of the patient support during said automatic shadow image generating mode, and said number of individual measurement readings being at least two hundred and forty-two.

33. Tomographic apparatus according to claim 29, with said patient support having location measurement means for identifying the longitudinal position of the patient support relative to said X-ray measurement arrangement, and image display means coupled with said shadow image storage means for visually reproducing an X-ray shadow image of the patient based on the successive sets of measurement readings produced in said automatic shadow image generating mode and visually displaying, along with the X-ray shadow image, means for identifying the respective longitudinal positions of respective segments of the displayed X-ray shadow image in relation to said X-ray measurement arrangement.

34. Tomographic apparatus for the production of transverse-layer images of a patient, comprising
   (a) a patient support having a longitudinal direction,
   (b) an X-ray measuring arrangement including an X-ray source which produces a fan-shaped beam of X-ray energy for penetrating a patient transverse layer at a transverse plane, and radiation measurement means in said transverse plane which provides a set of measurement readings which are measures of the radiation intensity of the transmitted fan-shaped beam,
   (c) tomographic angular scanning means coupled with the X-ray source for producing rotational movements of said fan-shaped beam in said transverse plane through a wide range of angular relationships relative to the patient transverse layer so as to generate a sufficient number of sets of measurement readings to define a tomographic layer image of the patient transverse layer,
   (d) longitudinal scanning means operating in a shadow image generating mode for producing relative longitudinal movement between the measuring arrangement and the patient support in the longitudinal direction of the latter during storage of the measurement readings from the radiation measurement means, and including
   (e) control means operating in said shadow image generating mode for intermittently turning on said X-ray source such that the X-ray source is pulsed during the relative longitudinal movement of said patient support through successive relative longitudinal positions while the X-ray source is in a single angular relationship relative to said patient support, and
   (f) shadow image storage means operating in said shadow image generating mode for the storage of a set of measurement readings from the radiation measurement means in each of the successive relative longitudinal positions for defining an X-ray shadow image of the patient having a substantial transverse extent and having a longitudinal extent corresponding to the range of relative longitudinal movement produced by said longitudinal scanning means during operation of said control means in said shadow image generating mode,
   (g) said control means operating in said shadow image generating mode for correlating the frequency of the intermittent turning on of the X-ray source with the rate of operating of the longitudinal scanning means in producing said relative longitudinal movement such that said X-ray source is pulsed at said successive relative longitudinal positions which define said X-ray shadow image of the patient and such that said X-ray energy penetrates successive patient regions with the single angular relationship to said patient support at said successive relative longitudinal positions during the operation of said control means in said shadow image generating mode.

35. Tomographic apparatus according to claim 34, with said control means automatically turning on said X-ray source during operation in said shadow image generating mode with a frequency so correlated with said rate of relative longitudinal movement of said patient support that the X-ray source is pulsed only at successive relative longitudinal positions which are separated by a distance substantially corresponding to the transverse image resolution given by said radiation measurement means.

36. Tomographic apparatus according to claim 34, with said radiation measurement means comprising a bank of detectors which are successively offset from each other in a transverse direction for receiving said fan-shaped beam of X-ray energy from said X-ray source, the number of successively offset detectors of said bank providing a transverse image resolution in the transverse direction, said control means automatically turning on said X-ray source during operation in said shadow image generating mode with a frequency so correlated with said rate of relative longitudinal movement of said patient support that the X-ray source is pulsed only at successive longitudinal positions which are separated by a longitudinal increment substantially corresponding to said transverse image resolution given by said number of successively offset detectors of said bank.

37. Tomographic apparatus according to claim 36, with said bank of detectors having at least two hundred and forty-two individual detectors.

* * * * *